United States Patent [19]

Braidwood et al.

[11] Patent Number: 5,770,621
[45] Date of Patent: Jun. 23, 1998

[54] CONTROL OF SEA LICE IN FISH

[75] Inventors: Julian Charles Braidwood, Cumbria; Jayne Laura Hart, Helensburgh, both of United Kingdom

[73] Assignee: Grampian Pharmaceuticals Limited, Leyland, United Kingdom

[21] Appl. No.: 809,278

[22] PCT Filed: Sep. 8, 1995

[86] PCT No.: PCT/GB95/02153

§ 371 Date: Mar. 11, 1997

§ 102(e) Date: Mar. 11, 1997

[87] PCT Pub. No.: WO96/08138

PCT Pub. Date: Mar. 21, 1996

[30] Foreign Application Priority Data

Sep. 12, 1994 [GB] United Kingdom .................. 9418328

[51] Int. Cl.$^6$ .................................................. A61K 31/275

[52] U.S. Cl. ............................................................. 514/521
[58] Field of Search .............................................. 514/521

[56] References Cited

PUBLICATIONS

G.A. Boxhall et al. (EDS.), "Pathogens of wild and farmed fish. Sea Lice.", Ch. 17, pp. 219–252, 1994.
G.A. Boxhall et al. (EDS.), "Pathogens of wild and farmed fish. Sea Lice", Ch 20, pp. 275–289, 1994.

*Primary Examiner*—Raymond Henley, III
*Attorney, Agent, or Firm*—Dann, Dorfman, Herrell and Skillman

[57] ABSTRACT

The use of various pyrethroid compounds is disclosed for the treatment of the immature phases of sea lice in sea water fish, such as salmon, and for the prophylaxis of adult sea lice infestation in such fish. Cypermethrin, high-cis-cypermethrin, lambda-cyhalothrin and deltamethrin are shown to be most effective.

12 Claims, 5 Drawing Sheets

CONTROL OF SEA LICE IN FISH

This is a 371 of PCT/GB95/02153 filed Sep. 8, 1995.

This invention relates to the control of sea lice in fish, such as salmon.

Infestation of salmon with sea lice is a recognised problem. Salmon are infected by free swimming immature sea lice in the copeopodid phase of development, which attach themselves to the body of the fish by hooked antennas. Once attached to the fish, the lice develop through four immature chalimus phases before becoming pre-adults about 2–3 weeks after the initial infestation. During the chalimus phases, the lice attach themselves to the fish by frontal filaments, and though they feed on the fish, they do not cause extensive damage. During their final pre-adult and adult phases of development, the lice attach themselves to the body of the fish by suction and graze over its surface, especially the head, back and peri-anal areas, causing extensive damage and ultimately death.

A number of treatments have been used to control sea lice in the past, most notably dichlorvos, azamethiphos and hydrogen peroxide treatment baths. A common feature of these known treatments is that they are effective only against mature lice (i.e. lice in the pre-adult and adult phases), and are ineffective against lice in immature phases of development. Hydrogen peroxide has been suggested by some workers to have a limited effect against immature lice, but this effect is slight compared to its effect on mature lice.

The reason for this selective activity is not known but it is thought likely to be due in some way to the substantial differences in anatomy and metabolism between the immature (copeopodid and chalimus) and mature (pre-adult and adult) lice. One theory is that differences in respiration are responsible, but this has not been fully substantiated. Whatever the underlying reasons for the selectivity, it remains an empirical rule that the conventional topical treatments are effective only against mature lice, with the resultant drawback that infested fish require repeated and frequent treatments in order to kill the lice as and when they mature.

We have now identified a group of compounds that are effective for controlling immature as well as mature sea lice. The compounds concerned are the pyrethroids, for example Cypermethrin (3-(2,2-Dichloroethenyl)-2,2-dimethyl-cyclopropanecarboxylic acid cyano (3-phenoxyphenyl)-methyl ester). We have already suggested the use of these compounds for the control of sea lice in our international patent application, published as WO 92/16106, but it was previously thought that the compounds were effective only for mature lice, and the tests described in our earlier application utilised mature lice exclusively. Because of the known resistance of immature lice to all known conventional bath treatments for mature lice, the identification of a group of compounds which is effective when used topically against both mature and immature lice is surprising. It is also of significant practical importance, in that a single treatment will affect substantially all of the lice present on the fish, whether mature or immature, thereby reducing the frequency with which treatments need to be made. This in turn leads to a saving in labour, a decrease in environmental contamination, and the minimising of stress to the fish.

The present invention therefore provides the use of a pyrethroid compound for the manufacture of a composition for the treatment of the immature phases of sea lice infestation of fish.

Alternatively, the invention provides the use of a pyrethroid compound for the manufacture of a composition for the prophylaxis of pre-adult and adult sea lice infestation of fish.

The invention is hereinafter described by way of example only, with reference to the following experimental trials and the accompanying figures which illustrate the results of the trials.

TRIAL 1

Figure 1A:
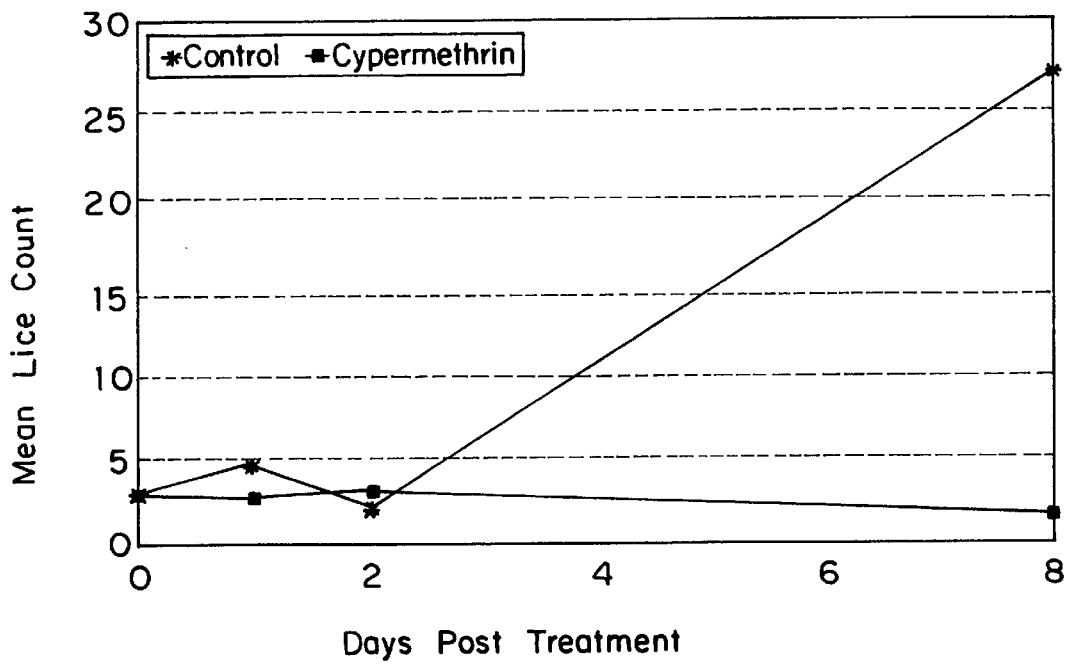
FIGS. 1, 2A, 2B, and 3 show the effectiveness of pyrethroids against the immature stages of sea lice.

Trial 1 was carried out at the Marine Harvest International research establishment at Loch Eil, Inverness-shire. The fish used in the trial were mixed sex Atlantic Salmon (*Salmo salar*), of the "Marine Harvest M6" strain, aged approximately 28 months, and weighing approximately 3 kg each.

Preparation 316 study fish were submitted to a pre-study veterinary examination and found to be suitable to participate in the study. The fish were held in a single holding cage in Loch Eil and were fed the same commercial fish feed (Fulmar Expanded Salmon Feed, Super Energy Salmon) for the ten days leading up to the study period, and throughout the duration of the study, therefore ensuring that no acclimatisation problems arose. Feed was thrown onto the surface of the water in the cage at a rate of approximately 0.5% bodyweight daily. On the day prior to treatment 15 fish were examined and counted for major phases of sea lice (chalimus, pre-adult and adult) and the mean counts taken as representative of the pre-treatment levels. The remaining 301 fish were then divided into six similar groups, five containing 50 fish each, and the sixth 51 (the extra fish resulted from a miscount, which was discovered during the trial, but was considered to be insignificant). Care was taken to ensure that all groups were as similar as possible in terms of weight and lice numbers.

Method

Each group of fish was placed in an individual experimental sea cage measuring 5m ×5m ×4m (depth) and constructed of nylon mesh nets. The cages were anchored in Loch Eil and open to the sea. Three of the groups were designated as treatment groups and three as control groups.

The treatment groups were each subjected to treatment with Cypermethrin at a concentration of 100 µg/l for one hour. During treatment, the bottoms of the cages were raised to give cage water depths of 2 meters. Impervious tarpaulins were used to surround individually each of the cages, and oxygen was diffused into the cages using a circular diffusor, to maintain an oxygen level of at least 8 mg/l during the time of treatment. Treatment was carried out by measuring an amount of 2.54 wt % stock solution of Cypermethrin calculated to give a final concentration in the cage of 100 µg/l, mixing this in a bucket of sea water, and then pouring this concentrated mixture into the appropriate cage, at several sites around the cage. After addition of treatment solution to the cages, the tarpaulins remained in place for 1 hour.

The method was repeated with the control cages, but without the addition of Cypermethrin.

Sampling and Measurements

Sampling was carried out by removing 10 fish from each tank, anaesthetizing the fish, and counting the number of chalimus, pre-adult and adult lice on each fish in accordance with the Marine Harvest International Standard Operating Procedure. The fish used for counting were killed, and not returned to the experimental cages. Counts were conducted at the following times:

Day of treatment (Day 1) : Approximately 1 hour after removal of the tarpaulin from the cage.

Day 2 Approximately 24 hours after removal of the tarpaulins from the cage.

Day 8

Day 15

Results

Figure 1B:
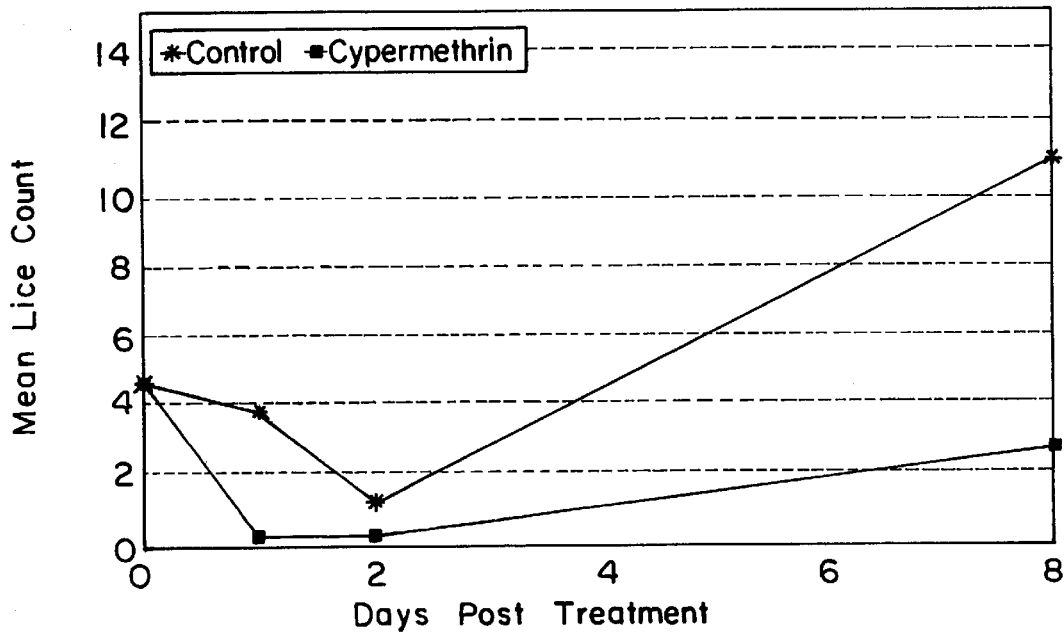
Figure 1C:
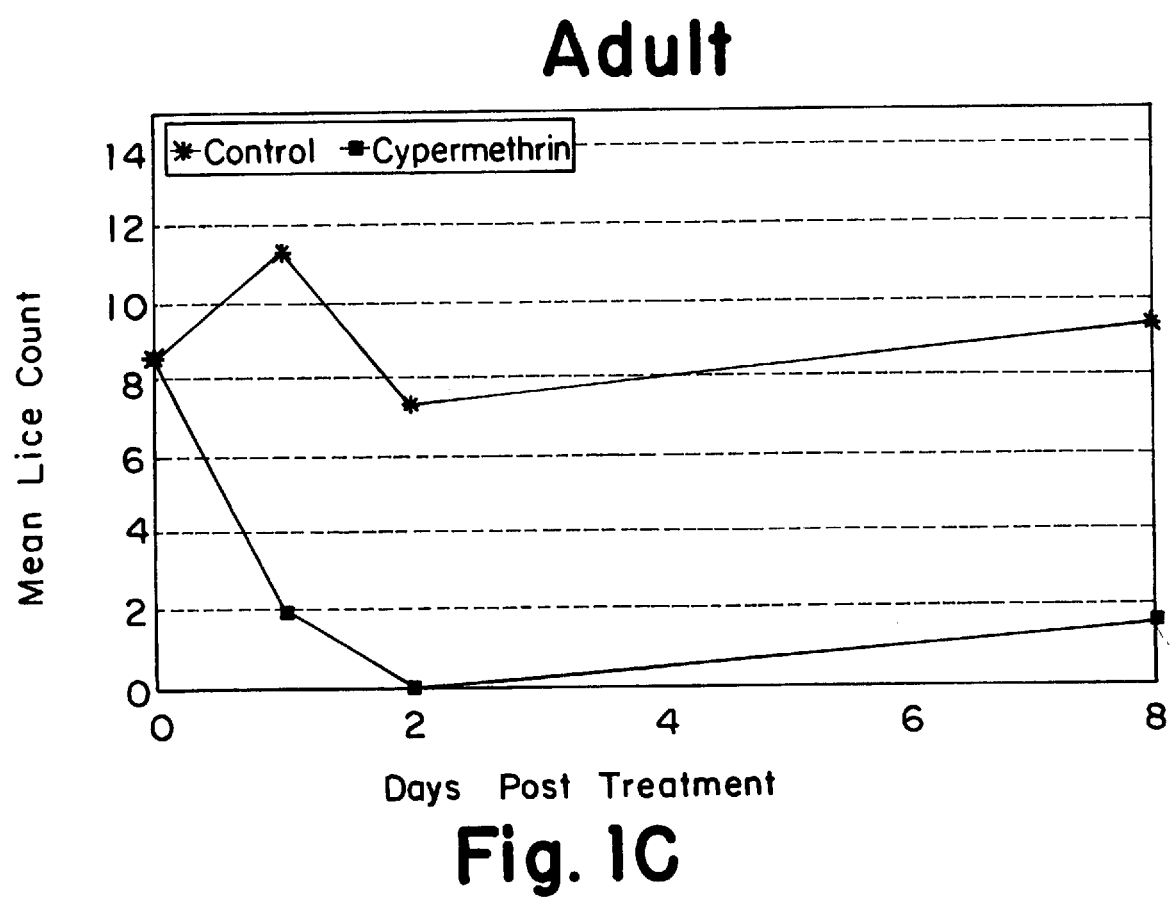

Table 1 below summarises the results obtained. (Where the number of lice on a fish was greater than 100, it was recorded as >100 and taken to equal 100 during data analysis.) The results are presented graphically in FIG. 1.

TABLE 1

| Treatment | Day | Mean number of lice (Standard deviation in parentheses) | | |
| --- | --- | --- | --- | --- |
| | | Chalimus | Pre-adult | Adult |
| PRE-TREATMENT | 0 | 3.13 (2.42) | 4.6 (1.99) | 8.6 (2.9) |
| CYPERMETHRIN | 1 | 2.97 (2.41) | 0.3 (0.6) | 1.93 (1.48) |
| CONTROL | 1 | 4.77 (1.89) | 3.82 (1.53) | 11.4 (4.26) |
| CYPERMETHRIN | 2 | 3.17 (2.16) | 0.23 (0.5) | 0.03 (0.18) |
| CONTROL | 2 | 2.2 (2.4) | 1.26 (1.31) | 7.3 (6.6) |
| CYPERMETHRIN | 8 | 1.33 (1.19) | 2.67 (2.47) | 1.5 (1.7) |
| CONTROL | 8 | 26.6 (16.2) | 10.9 (8.9) | 9.3 (5.5) |
| CYPERMETHRIN | 15 | 87.5 (20.6) | 77.8 (23.9) | 10.5 (7.1) |
| CONTROL | 15 | 90.3 (17.3) | 76.6 (25.5) | 22.2 (10.6) |

Each value = mean of 30 fish; Pre-treatment values = mean of 15 fish

Treatment with Cypermethrin at 100 μg/l for 1 hour substantially reduced chalimus, pre-adult and adult numbers of lice on treated fish, as compared to untreated fish. The effect was seen particularly at day 8 (7 days after treatment), but was substantially reduced by day 15. A possible explanation for this lack of difference on day 15 is that reinfection occurred from the untreated to treated fish; a massive sea lice infection of the site noted on day 8 could have contributed to rapid reinfection. When used commercially, all fish would be treated simultaneously, hence all lice would be affected, and so reinfection would not be expected to occur so soon after treatment.

The effect against adult and pre-adult lice was expected from our previous work described in WO 92/16106, but the significantly lower numbers of chalimus lice on treated fish 7 days after treatment (day 8) as compared to untreated fish was completely unexpected. The reasons for this effect are unknown, but it is suggested that the treatment killed a proportion of the chalimus lice, and also in some way stopped or delayed maturation of copeopodids into chalimus for several days. A second trial (Trial 2) was carried out in order to investigate the effect further:

TRIAL 2

Trial 2 was carried out at the Marine Harvest International Experimental Challenge Unit at Lochailort, Inverness-shire. Two studies were conducted; firstly, a pilot study (control) in which the rate of survival and development of sea lice on fish in a tank environment was investigated; and secondly a trial study to investigate the effect of Cypermethrin.

Method

In both pilot and trial studies, 60 Atlantic Salmon smolts were taken and challenged with a known number of sea lice copeopodids. The fish in the pilot study (referred to as GP1) were counted for lice at 10 days, 21 days and 27 days after initial infestation, while those in the trial study (referred to as GP2) were counted for lice at 10 days after infestation (immediately before treatment) and at 20 days and 28 days after infestation. Counting was carried out by killing 10 randomly chosen fish at each count, and examining and identifying stages of lice by use of a microscope. The number of lice in each of the following phases of development was recorded: Copeopodid, Chalimus I, Chalimus II, Chalimus III, Chalimus IV, Pre-Adult I, Pre-Adult II and Adult.

Treatment of the fish in trial study GP2 was for one hour with trial solution GPRDO1 containing Cypermethrin at a final concentration of 5 μg/l of seawater.

Results

Figure 2A:
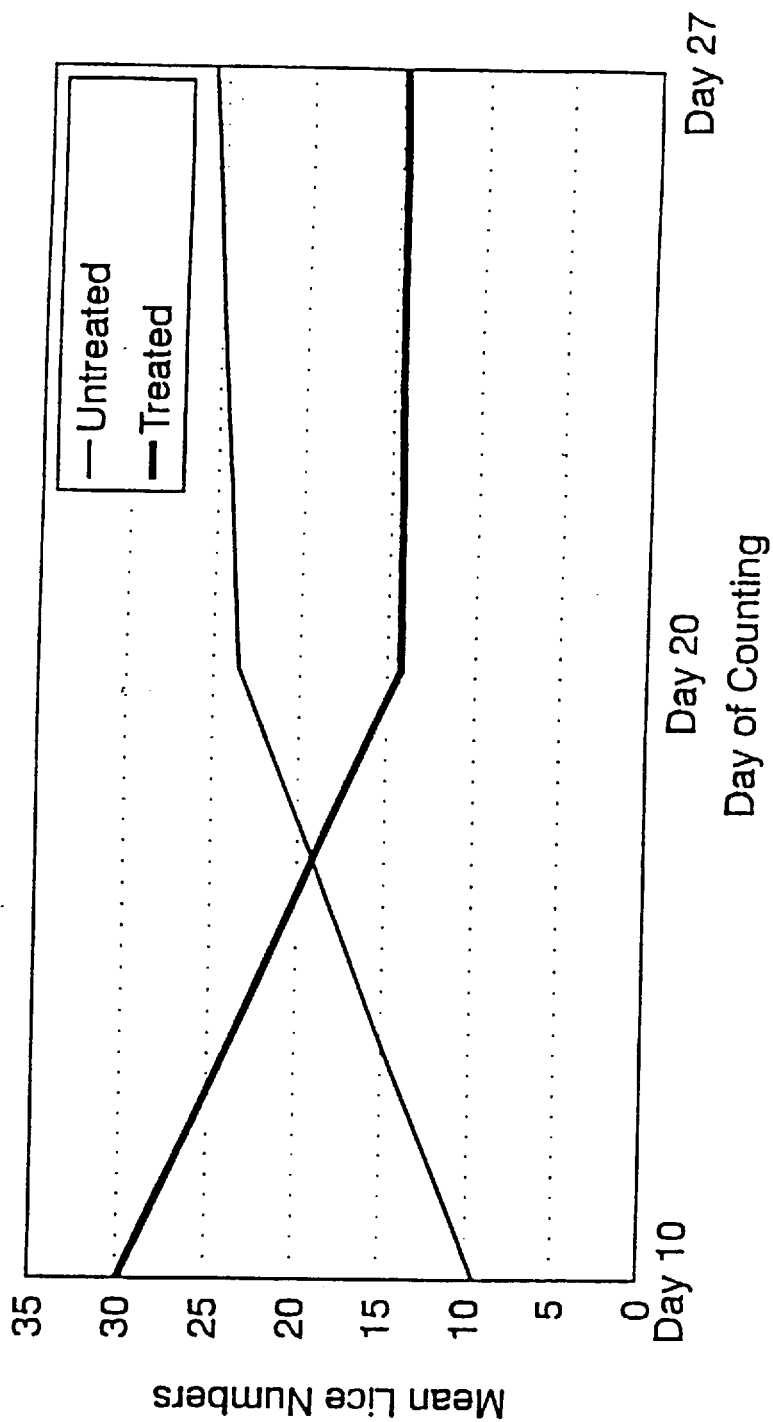

The mean total lice counts for the two studies are set out below in Table 2, and are presented graphically in FIG. 2A.

TABLE 2A

| Lice Numbers | Untreated Group (GP1) | Treated Group (GP2) |
| --- | --- | --- |
| Number of copeopodids used for challenge | 3,500 | 9,500 |
| Post-challenge Count 1 (+10 days) | 9.5 | 29.9 (before treatment) |
| Post-challenge Count 2 | 23.5 (+21 days) | 14.2 (+20 days) |
| Post-challenge Count 3 | 25.7 (+27 days) | 14.7 (+28 days) |

Figure 2B:
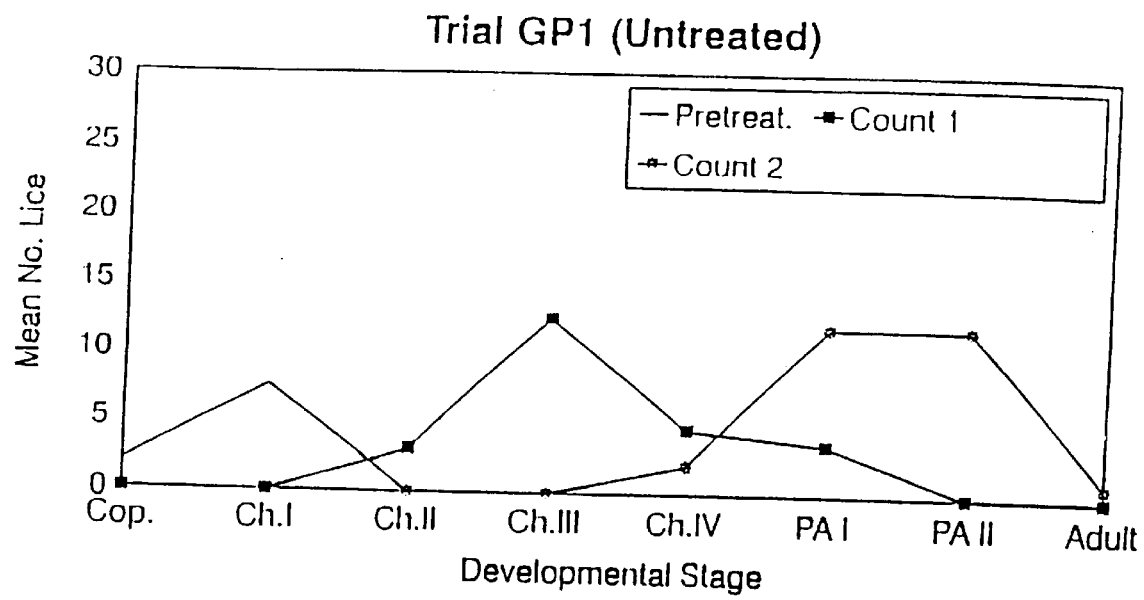
Figure 2C:
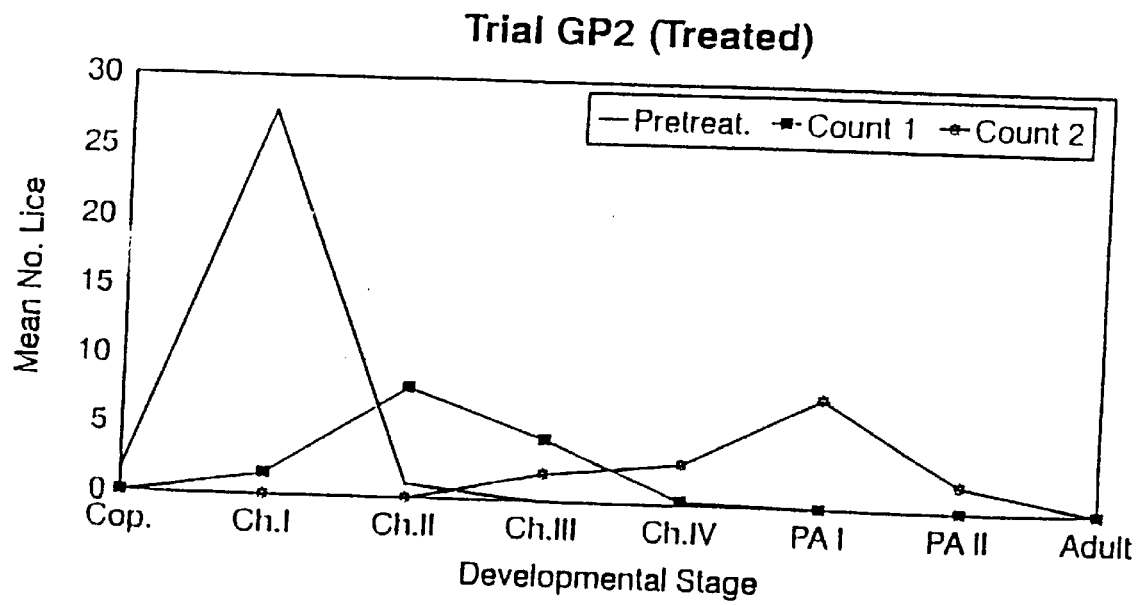

Tables 2B and 2C below indicate the percentages of total sea lice observed in each developmental phase, the results being represented graphically in FIG. 2B.

TABLE 2B

Pilot Study GP1 - sea lice development (untreated)

| Lice Stage | 10 days post infestation | 21 days post infestation | 27 days post infestation |
| --- | --- | --- | --- |
| Copeopodids | 21% | | |
| Chalimus I | 79% | | |
| Chalimus II | | 13% | |
| Chalimus III | | 53% | |
| Chalimus IV | | 19% | 7% |
| PreAdult 1 | | 15% | 46% |
| PreAdult 2 | | | 46% |
| Adult | | | 0.4% |

TABLE 2C

Trial Study GP2 - seal lice development treated with GPRD01 10 days after infestation

| Lice Stage | 10 days post infestation | 20 days post infestation | 28 days post infestation |
| --- | --- | --- | --- |
| Copeopodids | 6% | | |
| Chalimus I | 92% | 12% | |
| Chalimus II | 2% | 54% | |
| Chalimus III | | 32% | 12% |
| Chalimus IV | | 2% | 16% |
| PreAdult 1 | | | 59% |
| PreAdult 2 | | | 13% |
| Adult | | | |

The results show a marked retardation in lice development when treated with Cypermethrin.

Ambient water temperature during pilot study GP1 (range 8.0 to 10.5° C.) was slightly lower than that during trial study GP2 (range 8.5 to 11.5° C.). This difference would be expected to cause GP2 lice to survive slightly better and develop slightly faster than GP1 lice, with the result that the differences in lice numbers and growth rates between treated and untreated populations would be likely to be ever greater if comparative trials were carried out in exactly similar conditions.

During pilot study GP1 the damage caused to the salmon by the sea lice was noted to be moderate to severe, and the extent of the damage was as would be expected in a natural situation. Some of the untreated fish were suffering with such severe lesions caused by the sea lice by 28 days after infestation that all remaining fish were culled for welfare reasons. In contrast, the fish used in trial GP2 had suffered no significant damage by day 28, when the last fish were culled for sea lice counting.

TRIAL 3

Trial 3 was carried out at a seawater site in the Faroe Islands, using hexagonal "Bridgestone" cages having a circumference of approximately 102 m and a depth in the order of 10 to 12.5 m.

Approximately 200,000 Atlantic Salmon (*Salmo salar*) of average weight 0.96 kg were used in the trial, and were divided between two treatment cages (A and B).

On day 0 of the trial, the nets of cage B were raised to a depth shallow enough to allow a tarpaulin to be placed underneath. Oxygen was dispersed into the cage to maintain an oxygen level greater than 7 mg/l. The tarpaulin was then used to enclose the cage volume to create a bath for treatment. The actual depth was measured by taking a boat out to the centre of the cage and dropping a weighted rope, which indicated a depth of approximately 4 meters to the tarpaulin.

Cage B was then treated with 700 liters of seawater as a negative control treatment to assess the effect, if any, of the experimental conditions of the fish. The tarpaulin was removed after 60 minutes.

The next day the fish mortalities were recorded and not found to be significantly higher than before the negative control treatment.

On day 1 of the trial, both cages were treated with a dose of 1% w/v cypermethrin, by mixing the required amount (500 ml) with 700 liters of seawater and applying, using a pump, to each cage. The final concentration of cypermethrin was found by analysis to be approximately 0.9 $\mu$g/l in each cage. The cages remained enclosed for 60 minutes and the oxygen levels were monitored.

On each day on which lice counts were taken, five fish were removed from each cage, killed by an overdosage of benzocaine and placed in individual labelled polythene bags. The fish were then frozen and stored for lice counting. Thi was done on day 0 and day 1 (pre-treatment) and on days 2, 8 and 14 (post-treatment).

Results

The culled fish were counted for *Lepeophtheirus salmonis* sea lice in the following stages of development: Chalimus I–II, Chalimus III–IV, pre-adult, adult, and gravid female. The numbers of *Caligus elongatus* sea lice were also counted. Mean values are set out in tables 3A and 3B below:

TABLE 3A (Tank A)

| Day | Chalimus I–II | Chalimus III—IV | Pre-Adults | Adults | Gravid females | Caligus |
|---|---|---|---|---|---|---|
| 1 | 2.80 | 2.40 | 1.40 | 1.80 | 1.00 | 0.60 |
| 2 | 0.20 | 0.20 | 0.20 | 3.40 | 1.60 | 0.00 |
| 8 | 0.00 | 0.60 | 0.00 | 1.00 | 1.00 | 0.00 |
| 15 | 1.20 | 0.80 | 0.20 | 0.80 | 0.40 | 0.00 |

TABLE 3B (Tank B)

| Day | Chalimus I–II | Chalimus III—IV | Pre-Adults | Adults | Gravid females | Caligus |
|---|---|---|---|---|---|---|
| 0 | 1.80 | 1.20 | 2.00 | 2.60 | 3.40 | 1.20 |
| 1 | 3.80 | 2.20 | 1.60 | 3.80 | 3.80 | 0.80 |
| 2 | 0.20 | 0.40 | 0.00 | 1.40 | 2.40 | 0.00 |
| 8 | 0.20 | 0.00 | 0.00 | 0.60 | 1.20 | 0.00 |
| 15 | 1.40 | 0.40 | 0.00 | 0.40 | 1.00 | 0.00 |

Figure 3:
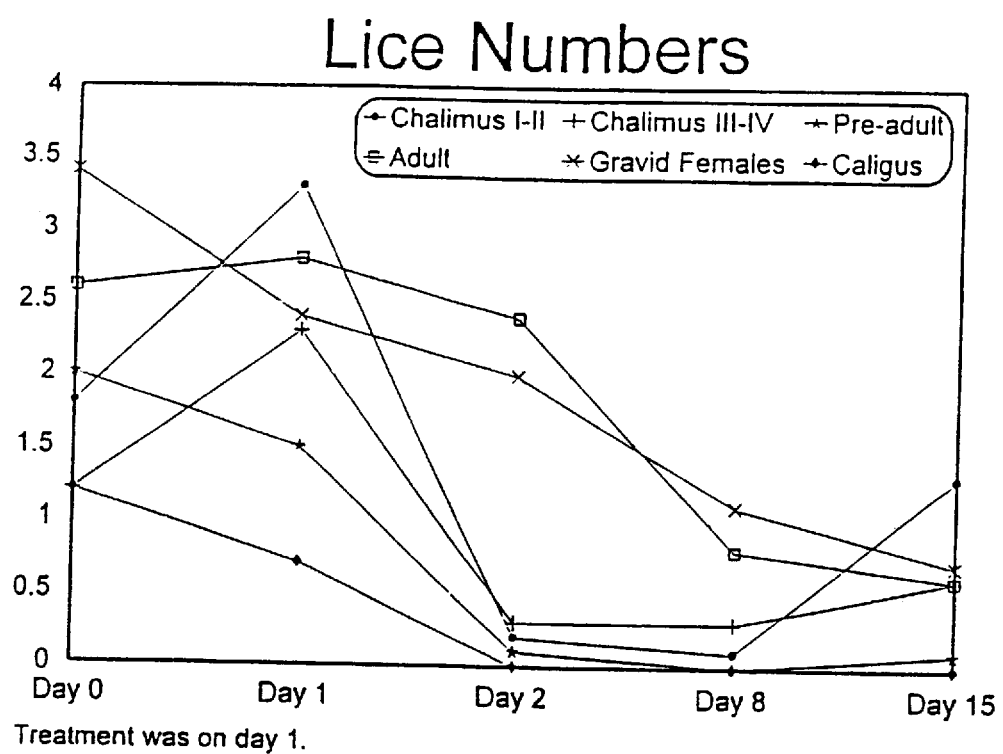

The mean results from tanks A and B are set out in table 3C below, and are illustrated graphically in FIG. 3.

TABLE 3C (Mean of Tanks A & B)

| Day | Chalimus I–II | Chalimus III—IV | Pre-Adults | Adults | Gravid females | Caligus |
|---|---|---|---|---|---|---|
| 0 | 1.80 | 1.20 | 2.00 | 2.60 | 3.40 | 1.20 |
| 1 | 3.30 | 2.30 | 1.50 | 2.80 | 2.40 | 0.70 |
| 2 | 0.20 | 0.30 | 0.10 | 2.40 | 2.00 | 0.00 |
| 8 | 0.10 | 0.30 | 0.00 | 0.80 | 1.10 | 0.00 |
| 15 | 1.30 | 0.60 | 0.10 | 0.60 | 0.70 | 0.00 |

Statistical Analysis of Results

The lice counts were logarithmically transformed and analysed using parametric statistical methods. In particular, the pre-treatment counts before and after the negative control were analysed by using a two-sample t-test. The results of this test are in Table 3D below:.

TABLE 3D

| Day | Chalimus I–II | Chalimus III—IV | Pre-Adults | Adults | Gravid Females | *Caligus* elongatus |
|---|---|---|---|---|---|---|
| T-value | −2.88 | −1.41 | 0.83 | −0.94 | 0.50 | 0.88 |
| p-value | 0.024 | 0.200 | 0.44 | 0.38 | 0.64 | 0.41 |
| significance | Significant | Not significant | Not significant | Not significant | Not significant | Not significant |

Significance level = 0.05 (5%)

The negative control did not have a significant effect on the lice numbers of any of the life stages of *Lepeoptheirus salmonis* or *Caligus elongatus,* with the exception of the Chalimus I–II stages, this was in fact a statically significant increase in numbers. This may suggest the fish were being continually re-infected with a new generation of lice. (This possible effect was seen between day 8 and 14 post-treatment).

Pre-treatment counts and post-treatment counts were analysed using a randomised block design with cages as blocks. This analysis provided a test for significant differences between counts at different points in time. The results are displayed in Table 3E below:

TABLE 3E

| Day | Chalimus I–II | Chalimus III—IV | Pre-Adults | Adults | Gravid Females | *Caligus elongatus* |
|---|---|---|---|---|---|---|
| p-value | 0.001 | 0.026 | 0.002 | 0.239 | 0.111 | 0.001 |
| for day significance | Significant | Significant | Significant | Not significant | Not significant | Significant |

Significance level = 0.05 (5%).

*Caligus elongatus* and *Lepeoptheirus salmonis* phases Chalimus I to IV and pre-adult were significantly reduced using cypermethrin.

A significant time difference effect was found, so a Newman-Keuls multiple range test was used to make pairwise comparisons between counts at different points in time. The results are as follows:

Chalimus I–II

There were statistically significant differences (at a 5% significance level, i.e. there is only a 5% chance of finding these results in random data) between days 1 & 2; and 1 & 8. This would indicate a reduction in numbers at day 2, and then an increase in lice numbers between days 8 & 14. This is most likely due to a reinfestation of a new generation of lice.

Chalimus III–IV

There were statistically significant differences (5%) between days 1 & 2; 1 & 8; and 1 & 14.

Pre-adults

There were statistically significant differences (5%) between days 1 & 2; 1 & 8; and 1 & 14.

Adults

There were statistically significant differences (5%) between days 1 & 2; 1 & 8; and 1 & 14.

Gravid Females

There was no statistically significant reduction in gravid female lice numbers.

*Caligus elongatus*

There were statistically significant differences (5%) between days 1 & 2; 1 & 8; and 1 & 14.

TRIAL 4

Method

Gravid Female lice were collected from Atlantic Salmon and incubated at 14° C. for 5 days until the eggs had hatched and developed through the naupilus stages to copeopodids. Approximately 100 copeopodids were added to each of seven beakers of 500 ml seawater. Pyrethroids were added to six beakers at a concentration of 5 $\mu$g pyrethroid/liter. One beaker was used as a control. All the beakers were maintained at 14° C. for one hour.

After one hour the beakers of lice were sieved through 500 $\mu$m plankton mesh, and the lice then rinsed in fresh seawater before being placed in clean beakers and seawater.

The lice were then assessed comparing with the control beaker. The following factors were used for assessment:

reaction to light, reaction to vibration, and reaction to shadow.

The reaction were classified as Good, Moderate, Poor and None with reference to the control.

Three sub-samples, each of 10 ml, were removed from each beaker. The total number of lice and the number of mobile lice were recorded and displayed as a percentage.

An assessment was made for each beaker at 1 hour, 24 hours and 72 hours.

This experiment was then repeated at a later date, with different copeopodids at a higher concentration of 50 $\mu$m pyrethroid/ litre. This time the experiment was performed blind, to avoid bias by the observer.

| | Results | | | | | | | |
|---|---|---|---|---|---|---|---|---|
| | 5 $\mu$G PYRETHROID/LITER | | | | 50 $\mu$G PYRETHROID/LITER | | | |
| | LIGHT | VIBRATION | SHADOW | % MOBILE | LIGHT | VIBRATION | SHADOW | % MOBILE |
| 1 HOUR | | | | | | | | |
| Control | Good | Good | Good | 90 | Good | Good | Good | 80.6 |

Results

| | 5 μG PYRETHROID/LITER | | | | 50 μG PYRETHROID/LITER | | | |
|---|---|---|---|---|---|---|---|---|
| | LIGHT | VIBRATION | SHADOW | % MOBILE | LIGHT | VIBRATION | SHADOW | % MOBILE |
| Flumethrin | Moderate | Good | Moderate | 93 | None | None | None | 0 |
| Permethrin | Moderate | Moderate | Moderate | 86 | Moderate | Moderate | Moderate | 36.4 |
| Bifenthrin | Moderate | Good | Good | 90 | N/A | N/A | N/A | N/A |
| High-cis-cypermethrin | None | None | None | 0 | None | None | None | 0 |
| Cypermethrin | None | None | None | 0 | None | None | None | 0 |
| Deltamethrin | None | None | None | 0 | Good | Moderate | Good | 60 |
| Trebon | N/A | N/A | N/A | N/A | Good | Good | Good | 61.1 |
| Lambda-cyhalothrin | N/A | N/A | N/A | N/A | None | None | None | 0 |
| 24 HOURS | | | | | | | | |
| Control | Moderate | Good | Good | 93 | Good | Good | Good | 100 |
| Flumethrin | Good | Good | Good | 92 | Good | Good | Good | 18 |
| Permethrin | Good | Good | Good | 94 | Moderate | Good | Moderate | 87 |
| Bifenthrin | Moderate | Good | Good | 78 | N/A | N/A | N/A | N/A |
| High-cis-cypermethrin | None | Poor | Poor | 6 | None | None | None | 3 |
| Cypermethrin | None | Poor | Poor | 12 | None | None | None | 0 |
| Deltamethrin | None | Poor | Poor | 23 | None | None | None | 16 |
| Trebon | N/A | N/A | N/A | N/A | Poor | Poor | Moderate | 63 |
| Lambda-cyhalothrin | N/A | N/A | N/A | N/A | None | None | None | 19 |
| 72 HOURS | | | | | | | | |
| Control | Moderate | Good | Good | 83 | Good | Good | Good | 74 |
| Flumethrin | Moderate | Good | Good | 92 | Poor | Moderate | Moderate | 33 |
| Permethrin | Moderate | Good | Good | 80 | None | None | None | 0 |
| Bifenthrin | Moderate | Good | Good | 89 | N/A | N/A | N/A | N/A |
| High-cis-cypermethrin | None | Poor | Poor | 0 | None | None | None | 0 |
| Cypermethrin | None | Moderate | Moderate | 19 | None | None | None | 0 |
| Deltamethrin | None | None | None | 11 | None | None | None | 0 |
| Trebon | N/A | N/A | N/A | N/A | None | None | None | 28 |
| Lambda-cyhalothrin | N/A | N/A | N/A | N/A | None | None | None | 0 |

The results show that all pyrethroids appeared to have had some effect on the sea lice, although the results indicate a varying level of potency between different pyrethroids. Of the formulations tested lambda-cyhalothrin, high-cis-cypermethrin, cypermethrin and deltamethrin were the most efficacious.

It is a possibility that efficacy will vary with formulation as well as with pyrethroid. It was noted in the second experiment that the deltamethrin formulation did not mix well and formed oily droplets in the beaker. The pyrethroid formulations which mixed well and formed emulsions appeared to be effective immediately against the sea lice.

The bifenthrin was replaced in the second experiment with trebon and lambda-cyhalothrin. This was simply due to availability of the compounds.

Efficacy was assessed on the basis of decreased mobility of the lice, but there is no way of assessing if the lice are dead or merely immobile. It can be assumed, however, that if the immobile lice do not recover, they will not find a host, and will therefore die.

Conclusions

The results from Trial 1 show that Cypermethrin at a concentration of 100 μg/l substantially reduces not only the number of pre-adult and adult lice on the infested fish, as was expected, but also, surprisingly, the number of immature lice. Trial 2 shows that this effect is still marked when the concentration of Cypermethrin is reduced to 5 μg/l, and furthermore that the effect of the Cypermethrin is not only to reduce chalimus numbers by killing a portion thereof, but also to prolong development times of those which survive, thus delaying maturation to the most damaging pre-adult and adult phases. It is also thought that there may be an effect in reducing the feeding rate of the lice, thus reducing the damage caused by each individual surviving louse.

Trial 3 demonstrates that the effect of cypermethrin is still statistically significant, even at concentrations as low as 0.9 μg/l, and furthermore that it is effective not only against immature phases of *Lepeoptheirus salmonis*, but also against *Caligus elongatus*. It is anticipated that Cypermethrin will be effective in concentrations ranging from 0.05 μg/l to 500 μg/l, the concentration preferably being in the range 0.5 μg/l to 100 μg/l.

Trial 4 demonstrates the efficacy of other pyrethroid compounds, in particular lambda-cyhalothrin, high-cis-cypermethrin and deltamethrin.

It should be noted that the term "sea lice" is a general one, which applies to a number of different species of parasite, both of seawater and fresh water fish. It has been found in the past that effective treatments for one species are generally effective against other species also, and the invention therefore extends to the treatment of immature sea lice in general, regardless of species, and regardless of whether the infestations are of seawater or fresh water fish.

We claim:

1. A method for the treatment of the chalimus and copepodid phases of sea lice infestation of fish said method comprising administering to fish in need of said treatment a pyrethroid compound in an amount effective to reduce the number of said chalimus and copepodid phases of sea lice on the treated fish.

2. A method as claimed in claim 1, wherein said pyrethroid compound is selected from the group consisting of Cypermethrin, high-cis-cypermethrin, lambda-cyhalothrin or deltamethrin.

3. A method as claimed in claim 1, wherein said pyrethroid compound is topically administered to said fish.

4. A method as claimed in claim 2, wherein said pyrethroid compound is topically administered to said fish.

5. A method as claimed in claim 1, wherein said pyrethroid compound is administered in the form of a solution or suspension in a liquid vehicle.

6. The method as claimed in claim 2, wherein said pyrethroid compound is administered in the form of a solution or suspension in a liquid vehicle.

7. The method as claimed in claim 3, wherein said pyrethroid compound is administered in the form of a solution or suspension in a liquid vehicle.

8. A method as claimed in claim 6, wherein said solution or suspension contains said pyrethroid compound at a concentration of between 0.05 $\mu$g/l and 500 $\mu$g/l.

9. A method as claimed in claim 7, wherein said solution or suspension contains said pyrethroid compound at a concentration of between 0.05 $\mu$g/l and 500 $\mu$g/l.

10. A method as claimed in claim 8, wherein said concentration is between 0.5 $\mu$g/l and 100 $\mu$g/l.

11. A method as claimed in claim 9, wherein said concentration is between 0.5 $\mu$g/l and 100 $\mu$g/l.

12. A method for the prophylaxis of pre-adult and adult sea lice infestation of fish, said method comprising administering to fish in need of said prophylaxis a pyrethroid compound in an amount effective to retard said pre-adult and adult sea lice development in said fish.

* * * * *